US008634621B2

(12) United States Patent
Choi et al.

(10) Patent No.: US 8,634,621 B2
(45) Date of Patent: Jan. 21, 2014

(54) METHOD AND APPARATUS FOR OBTAINING PANORAMIC IMAGES

(75) Inventors: Seong-Il Choi, Gyeonggi-do (KR); Hyo Sung Cho, Gangwon-do (KR)

(73) Assignee: Vatech Co., Ltd., Gyeonggi-do (KR)

( * ) Notice: Subject to any disclaimer, the term of this patent is extended or adjusted under 35 U.S.C. 154(b) by 64 days.

(21) Appl. No.: 13/509,042

(22) PCT Filed: Nov. 10, 2010

(86) PCT No.: PCT/KR2010/007927
§ 371 (c)(1),
(2), (4) Date: May 10, 2012

(87) PCT Pub. No.: WO2011/059234
PCT Pub. Date: May 19, 2011

(65) Prior Publication Data
US 2012/0224762 A1 Sep. 6, 2012

(30) Foreign Application Priority Data
Nov. 10, 2009 (KR) .......................... 10-2009-0108098

(51) Int. Cl.
*G06K 9/00* (2006.01)
(52) U.S. Cl.
USPC ........................... 382/128; 382/132; 382/131
(58) Field of Classification Search
USPC ........................................ 382/128, 131, 132
See application file for complete search history.

(56) References Cited

U.S. PATENT DOCUMENTS

| | | | |
|---|---|---|---|
| 6,220,751 B1 * | 4/2001 | DiGiacomo et al. ........... | 378/182 |
| 6,493,415 B1 * | 12/2002 | Arai et al. ......................... | 378/4 |
| 6,587,542 B1 * | 7/2003 | Allen ............................ | 378/98.8 |
| 6,856,350 B2 * | 2/2005 | Orava et al. ..................... | 348/308 |
| 7,929,661 B2 * | 4/2011 | Borghese et al. ............... | 378/38 |
| 8,223,915 B2 * | 7/2012 | Borghese et al. ............... | 378/25 |
| 8,363,780 B2 * | 1/2013 | Loustauneau et al. .......... | 378/38 |
| 2002/0196895 A1 * | 12/2002 | Plotz .............................. | 378/21 |

(Continued)

FOREIGN PATENT DOCUMENTS

| JP | 2002-034973 A | 2/2002 |
|---|---|---|
| JP | 2006-314774 A | 11/2006 |

(Continued)

OTHER PUBLICATIONS

PCT International Search Report, Korean Intellectual Property Office, Jun. 28, 2011.

*Primary Examiner* — Tom Y Lu
(74) *Attorney, Agent, or Firm* — IP Legal Services, LLC (57) ABSTRACT

The present invention provides an apparatus and a method for obtaining panoramic images in which cervical effect is corrected in such a manner that the uniform contrast is shown. According to the apparatus and the method, the method comprises the steps of: obtaining a preceding frame image by irradiating radiation on one certain section of an image layer trace on which the tooth trace of a subject is embodied; calculating a gray scale average value of pixels that are included within a predetermined reference region of the preceding frame image; comparing the calculated gray scale average value with a gray scale reference value that is calculated from a prepared sample image, and generating a radiation correction value corresponding to a difference value therebetween; and obtaining a succeeding frame image by irradiating strength-adjusted radiation on one section that is adjacent to the other section of an unknown layer trace, according to the calculated radiation correction value.

15 Claims, 11 Drawing Sheets

(56) References Cited

U.S. PATENT DOCUMENTS

2006/0132750 A1 6/2006 Gui et al.
2009/0245461 A1* 10/2009 Lee .................................. 378/38
2010/0054403 A1 3/2010 Ro et al.

FOREIGN PATENT DOCUMENTS

| KR | 10-2009-0077025 A | 7/2009 |
|----|-------------------|--------|
| WO | 2007-110465 A1 | 10/2007 |
| WO | 2008-119873 A1 | 10/2008 |

* cited by examiner

METHOD AND APPARATUS FOR OBTAINING PANORAMIC IMAGES

CROSS REFERENCE TO RELATED APPLICATIONS

This application is a National Stage Patent Application of PCT International Patent Application No. PCT/KR2010/007927 (filed on Nov. 10, 2010) under 35 U.S.C. §371, which claims priority to Korean Patent Application No. 10-2009-0108098 (filed on Nov. 10, 2009), the teachings of which are incorporated herein in their entireties by reference.

TECHNICAL FIELD

The present invention relate to a method and an apparatus for obtaining a panoramic image, and more particularly, to a method and an apparatus for obtaining a panoramic image having a wholly uniform contrast by adjusting intensity of radiation irradiated to a subject so as to maintain gray scales of a frame image at a certain level.

BACKGROUND ART

Figure 1:
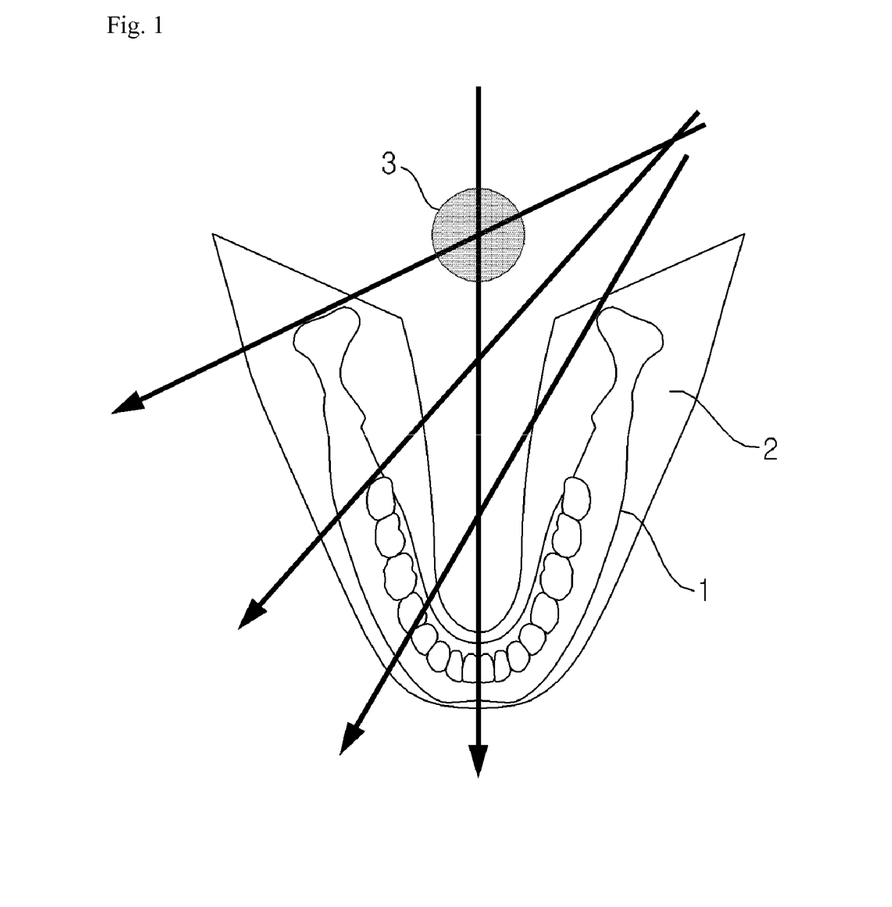
FIG. 1 is an exemplary diagram illustrating irradiation of radiation to a subject so as to obtain a panoramic image.

A panoramic image means an image obtained by previously setting an image layer trace to be obtained, photographing the images along the trace, and then, linking the obtained images. Generally, as illustrated in FIG. 1, an apparatus for obtaining a panoramic image obtains the panoramic image by reconstructing images obtained by irradiating radiation such as X-rays, or the like, to image layer traces where a region of interest 2 of a subject is located.

An apparatus for obtaining oral a panoramic image according to the related art is focused to a subject, an arch shape, when it rotates. Therefore, the apparatus for obtaining an oral panoramic image essentially scans a cervical spine 3 and brings out unbalance of contrast since X-rays are reduced at the time of obtaining images of anterior teeth due to the cervical spine.

When diagnosing a patient's state with the image having the non-uniform contrast, it is difficult to accurately determine the state of the arch that appears being overlapped with the cervical spine 3 portion darker than a peripheral portion thereof due to a cervical effect.

A wrong operation may be performed on a patient when a misdiagnosis is made about a patient's arch state due to the above problems, which is highly likely to cause medical accidents.

DISCLOSURE

Technical Problem

An embodiment of the present invention is directed to a method and an apparatus for obtaining panoramic images including an area sensor receiving radiation irradiated to an image layer trace where a region of interest of a subject is located, and for adjusting intensity of radiation so as to make gray scales of frame images to be obtained by the area sensor uniform.

Technical Solution

In accordance with an embodiment of the present invention, there is provided a method for obtaining panoramic images, including: a) obtaining a preceding frame image by irradiating radiation on any one section of an image layer trace in which a teeth trace of a subject is to be shaped; b) calculating a gray scale average value of pixels included in a predetermined reference area of the preceding frame image; c) comparing the calculated gray scale average value with a gray scale reference value calculated from a previously provided sample image, and generating a radiation correction value corresponding to a difference value; and d) obtaining a succeeding frame image by irradiating intensity-adjusted radiation on another section adjacent to the one section of the image layer trace according to the calculated radiation correction value.

The gray scale reference value is calculated by averaging the gray scale values of the pixels included in a predetermined reference area of a part except a cervical portion among the sample image.

The step d) includes d1) adjusting tube current or tube voltage according to the calculated radiation correction value; and d2) photographing the succeeding frame image by irradiating the intensity-adjusted radiation to the image layer trace according to the adjusted tube current or tube voltage.

This method further includes, after the step d), obtaining a plurality frame images by repeating steps b) to d) until a final frame image for a final section of the image layer trace is obtained; and generating the panoramic images by reconstructing the plurality of obtained frame images or, after the step d), e) linking the succeeding frame images to the preceding frame images; and generating the panoramic images by repeating steps b) to e) until a final frame image for a final section of the image layer trace is obtained.

At the step c), when the difference value deviates from a predetermined tolerable range, the radiation correction value corresponding to the difference value is calculated.

At the step c), when the difference value is in the tolerable range, at step d), the succeeding frame images are photographed by irradiating radiation having the same intensity as the radiation intensity irradiated at step a).

The reference area is located under a lower jaw in the frame images.

The image layer trace is provided in a plural by being divided into at least two sections, and wherein the obtaining of the preceding frame images includes: irradiating radiation on the plurality of image layer traces; selecting a section optimal image layer trace closed to a focal trace among the plurality of image layer traces belonging to each section; and obtaining the frame images for the selected section optimal image layer trace.

The sample images are provided in plural according to each category of subject information including age, weight, sex, nationality, race, computation, and case history of the subject, and the gray scale reference value is selected from the plurality of gray scale reference values each calculated from the plurality of sample images.

An apparatus for obtaining panoramic images includes: a radiation irradiator to irradiate radiations to a plurality of image layer traces forming an irradiation trace of radiation for a subject; an image sensor to receive radiations transmitting the plurality of image layer traces to obtain frame images for the plurality of image layer traces; a radiation dose adjustor to receive the frame images from the image sensor, to calculate a radiation correction value for adjusting a intensity of radiation to be irradiated at the time of photographing succeeding frame images by using the received frame images, and to adjust tube current or tube voltage applied to the radiation irradiator according to the radiation correction value; and an image processor to generate a panoramic image of the image layer traces by receiving and reconstructing the frame images obtained from the image sensor.

The radiation dose adjustor includes: an average value calculator to calculate a gray scale average value of pixels included in predetermined reference area among the obtained frame image; a correction value calculator to compare the calculated gray scale average value with previously provided sample images and to calculate a radiation correction value corresponding to a difference value when the difference value deviates from a predetermined tolerable range; and an intensity adjustor to adjust tube current or tube voltage according to the calculated radiation correction value.

The image sensor is an area sensor that obtains images in a frame unit by intermittently irradiating radiation.

The apparatus further includes: an adjust module to adjust the radiation irradiator so as to irradiate the radiation on each section of the image layer trace and to adjust the image sensor so as to receive the irradiated radiation by interworking the radiation irradiator.

The image processor includes: a trace selector to divide the plurality of image layer traces into at least two sections and to select, for each section, a section optimal image layer trace closed to a focal trace among the plurality of image layer traces belonging to each section; a final trace completion unit to link all of the selected section optimal image layer traces to complete a final trace; and an image reconstruction unit to link the panoramic images for the final trace.

Advantageous Effects

In accordance with the embodiments of the present invention, it is possible to obtain a panoramic image showing a uniform contrast by correcting the cervical effect. In addition, it is possible to reduce the occurrence of misdiagnosis and medical accidents by accurately diagnosing the patient's state using the panoramic image having the uniform contrast.

Best Mode

A panoramic image is formed by obtaining a preceding frame image by irradiating radiation on any one section of an image layer trace in which a teeth trace of a subject is to be shaped, calculating a gray scale average value of pixels included in a predetermined reference area of the preceding frame image, comparing the calculated gray scale average value with a gray scale reference value calculated from a previously provided sample image to generate a radiation correction value corresponding to a difference value, and obtaining a succeeding frame image by irradiating the radiation having the intensity-adjusted according to the calculated radiation correction value on other section adjacent to the one section of the image layer trace.

Mode for Invention

Hereinafter, exemplary embodiments of the present invention will be described in detail with reference to the accompanying drawings. In the specification, in adding reference numerals to components throughout the drawings, it is to be noted that like reference numerals designate like components even though components are illustrated in different drawings. The detailed descriptions of the components will be omitted when it is determined that the detailed descriptions of them may obscure the issue of the present invention.

Figure 2:
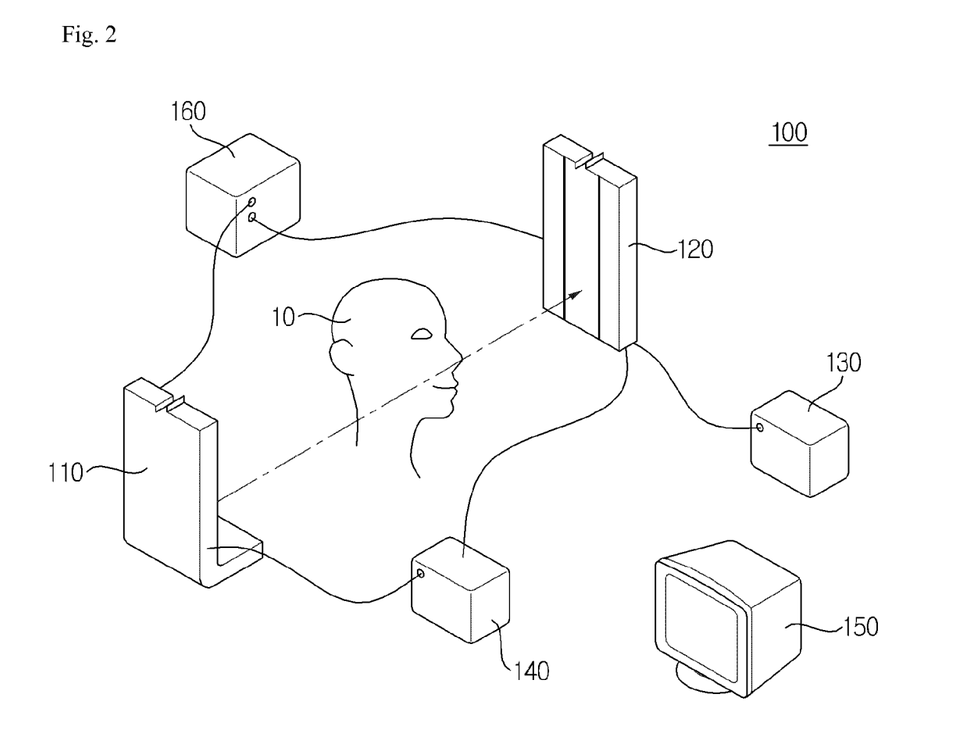
FIG. 2 is a schematic configuration diagram of an apparatus for obtaining a panoramic image in accordance with an exemplary embodiment of the present invention.

Hereinafter, an apparatus 100 for obtaining a panoramic image in accordance with an exemplary embodiment of the present invention will be described with reference to FIG. 2.

The apparatus 100 for obtaining a panoramic image in accordance with the exemplary embodiment of the present invention may include a radiation irradiator 110, an image sensor 120, a radiation dose adjustor 130, an image processor 140, and a display unit 150.

Figure 3:
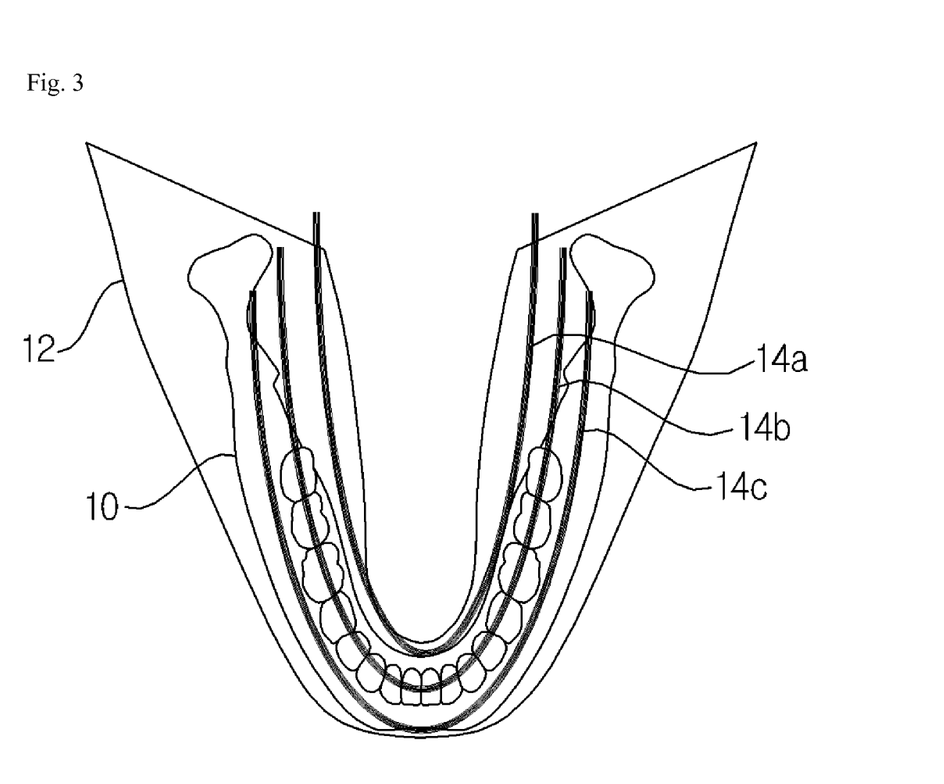
FIG. 3 is a schematic diagram illustrating image layer traces and a region of interest.

The radiation irradiator 110 may irradiate radiation while rotating around a subject 10 along a predetermined trace. In this case, the radiation irradiator 110 may irradiate radiation to a plurality of image layer trajectories 14a, 14b, and 14c where a region of interest 12 of the subject 10 is located and a teeth trace of the subject 10 is to be shaped, as illustrated in FIG. 3. Here, the region of interest means a portion of the inside of the subject 10 to be photographed. The radiation irradiator 110 may irradiate the radiation for each section of each image layer trace 14a, 14b, and 14c that are split into a plurality of sections, wherein the intensity of the irradiated radiation may be adjusted by the radiation dose adjustor 130 that adjusts tube current and tube voltage applied to the radiation irradiator 110. The radiation irradiated by the irradiator 110 may transmit subject 10 and be received by the image sensor 120 to obtain images for the subject 10. In this case, the radiation may be preferably X-rays or gamma rays having transmitting power enough to transmit a body.

Figure 4:
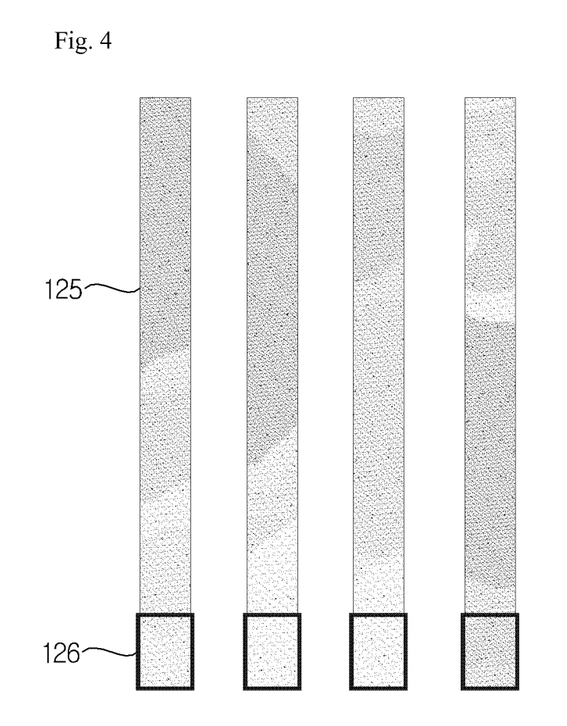
FIG. 4 is a schematic diagram illustrating each unit frame image for each section and a reference area for each unit frame image.

The image sensor 120, which is a sensor having a predetermined area, may be operated by interworking the radiation irradiator 110 with the subject 10 therebetween and may receive the radiation transmitting the image layer trace 14 to obtain images for the region of interest 12 of the subject 10 located in the image layer trace 14. Further, as illustrated in FIG. 4, the image sensor 120 may obtain the frame images 125 that are unit images by the radiation irradiated for each section of the image layer trace 14. The image sensor 120, which obtains the frame images 125 by the radiation intermittently irradiated rather than by consecutive scan photographing, may use only a part s1 of an image acquisition area S as illustrated in FIGS. 5 and 6.

Figure 5:
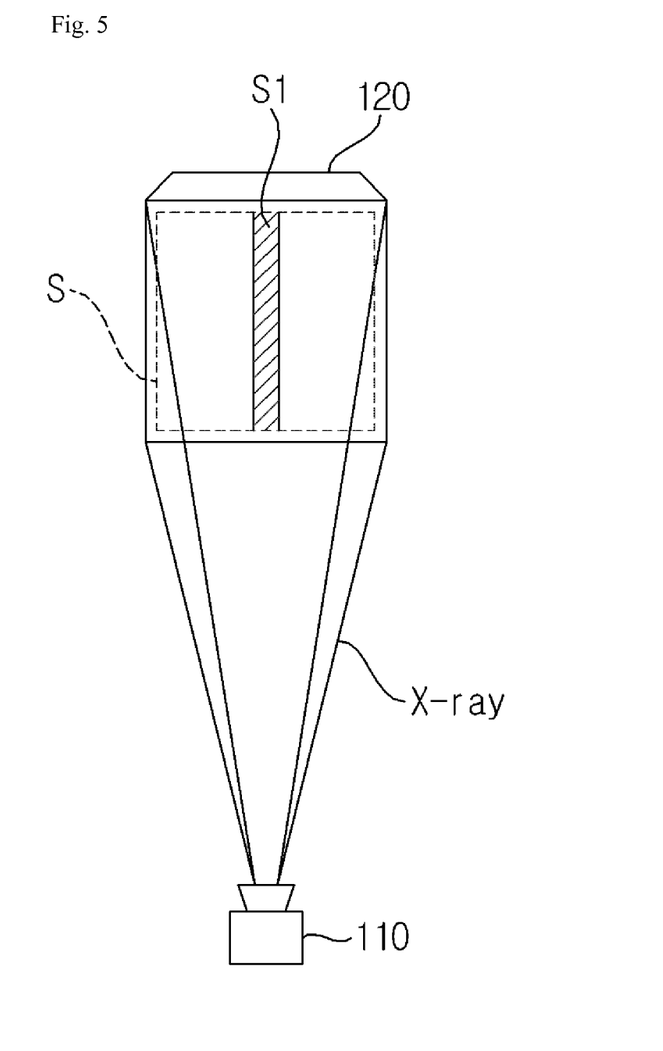
FIG. 5 is a diagram illustrating a state of receiving radiation of an active type image sensor.

Although X-rays are irradiated to the overall area of the image acquisition area S, a method of using the radiation acquired at only a part s1 of the image acquisition area S, is applied to the active type sensor illustrated in FIG. 5. By this method, only some area s1 is activated and the rest area is inactivated. Thus, radiation is received only at the activated area s1. For example, the active type sensor may be a sensor of a type that turns-on only some photosensitive elements corresponding to the area s1 among the photosensitive elements (not illustrated) configuring the image acquisition area s and turns-off the remaining photosensitive elements. Alternatively, the active type sensor may be a sensor of a type that activates the overall image acquisition area s but extract only the radiation images obtained by the some area s1. For example, a detecting unit (not illustrated) detects only data that are stored in the photosensitive elements corresponding to some area s1. In more detail, the image sensor 120 may include gate drivers (not illustrated) transferring the data stored in the photosensitive elements to the detecting unit and transfers only the data stored in the photosensitive elements corresponding to some area s1 to the detect unit with the gate drivers, such that the detecting unit can detect only the radiation images obtained by some area s1. In summary, the active type sensor is used in a method of extracting only the radiation images obtained by some area s1 independent of the irradiation range of the radiation.

Figure 6:
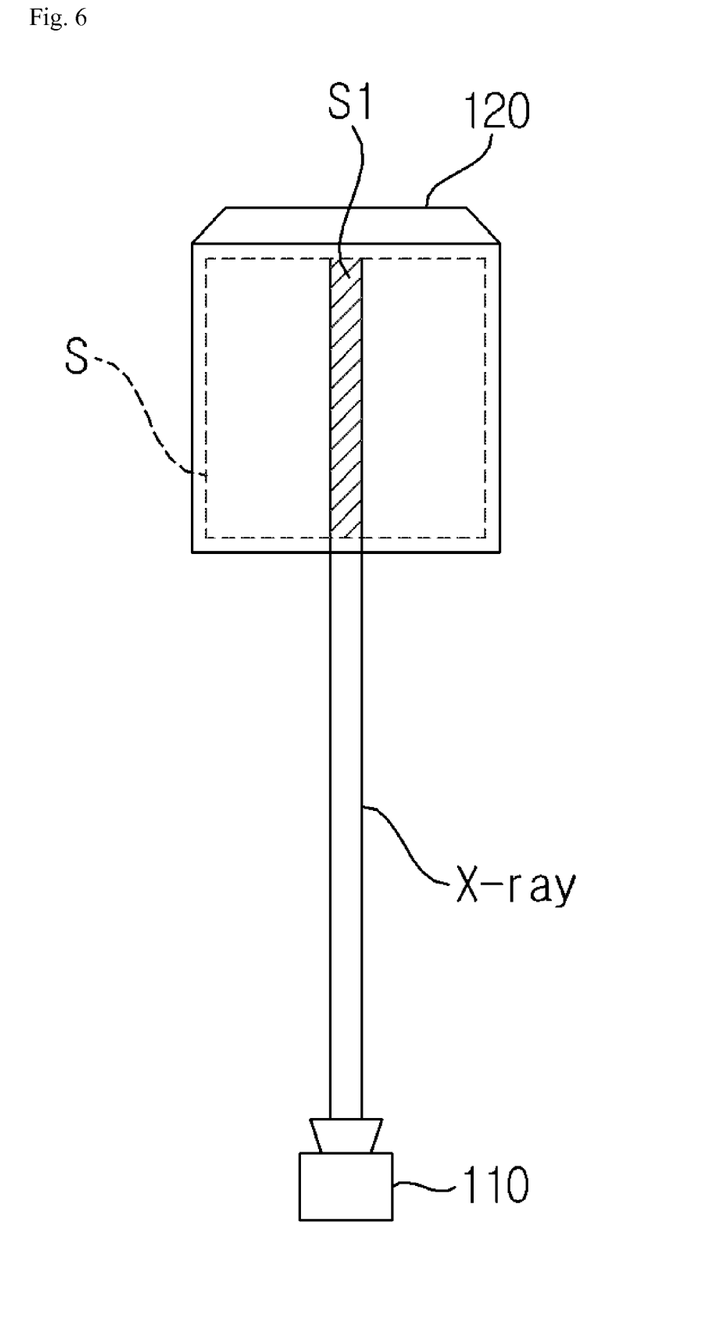
FIG. 6 is a diagram illustrating a state of receiving radiation of a passive type image sensor.

Meanwhile, the passive sensor illustrated in FIG. 6 is a type of allowing only some area s1 to obtain the radiation images by irradiating the radiation only to some area s1 of the image acquisition area s.

For example, the radiation irradiator 110 may include a slit (not illustrated) adjusting the irradiation range of the radiation and irradiate the radiation to only some area s1 of the image acquisition area s by adjusting the slit.

The image sensor 120 may be preferably implemented with a charge-coupled device (CCD) sensor or a complementary metal-oxide semiconductor (CMOS) sensor, however if the image sensor 120 is a sensor capable of receiving the radiation radiated from the radiation irradiator 110, any sensor may be used.

Figure 7:
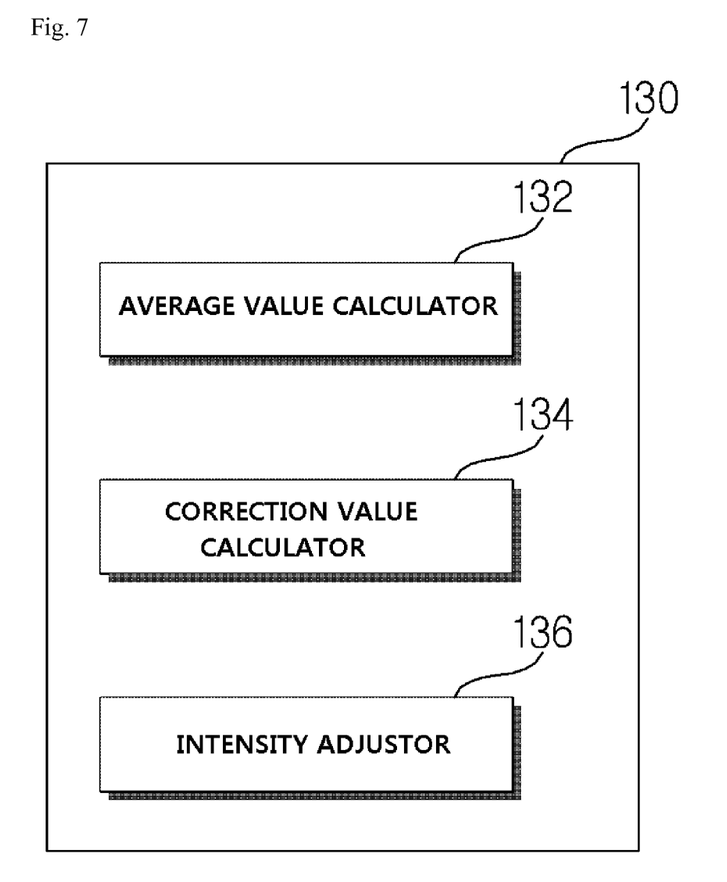
FIG. 7 is a block diagram illustrating a configuration of a radiation dose adjustor.

The radiation dose adjustor 130 may receive the image 125 obtained by the image sensor 120, calculate a radiation correction value for adjusting the intensity of radiation to be irradiated at the time of photographing a succeeding frame image 125 by using the received frame images 125, and adjust tube current or tube voltage applied to the radiation irradiator 110 according to the calculated radiation correction value. The radiation dose radiated from the radiation irradiator 110 may be adjusted by the radiation dose adjustor 130 to obtain the panoramic image having the uniform contrast. As illustrated in FIG. 7, the radiation dose adjustor 130 may include an average value calculator 132, a correction value calculator 134, and an intensity adjustor 136. The average value calculator 132 may calculate a gray scale average value of pixels of a predefined reference area 126 in each frame image 125 obtained from the image sensor 120. Here, the reference area 126 means an area including the plurality of pixels as the predetermined area corresponding to a part of the frame image 125. Preferably, as illustrated in FIG. 4, the reference area 126 may be set as an area including the plurality of pixels disposed under each frame image, that is, under the lower jaw. The average value calculator 132 may calculate a gray scale average value obtained by averaging the gray scale values of the pixels included in the reference area 126 and transmit the calculated gray scale average value to the correction value calculator 134. The correction value calculator 134 may compare the calculated gray scale average value with a gray scale reference value calculated from the previously provided sample images (not illustrated) and calculate the radiation correction value corresponding to a difference value when the difference value deviates from a predetermined tolerable range. The intensity adjustor 136 may receive the radiation correction value calculated from the correction value calculator 134 and adjust the intensity of the radiation to be emitted from the radiation irradiator 110 by adjusting the tube current or the tube voltage applied to the radiation irradiator 110 according to the radiation correction value.

Figure 8:
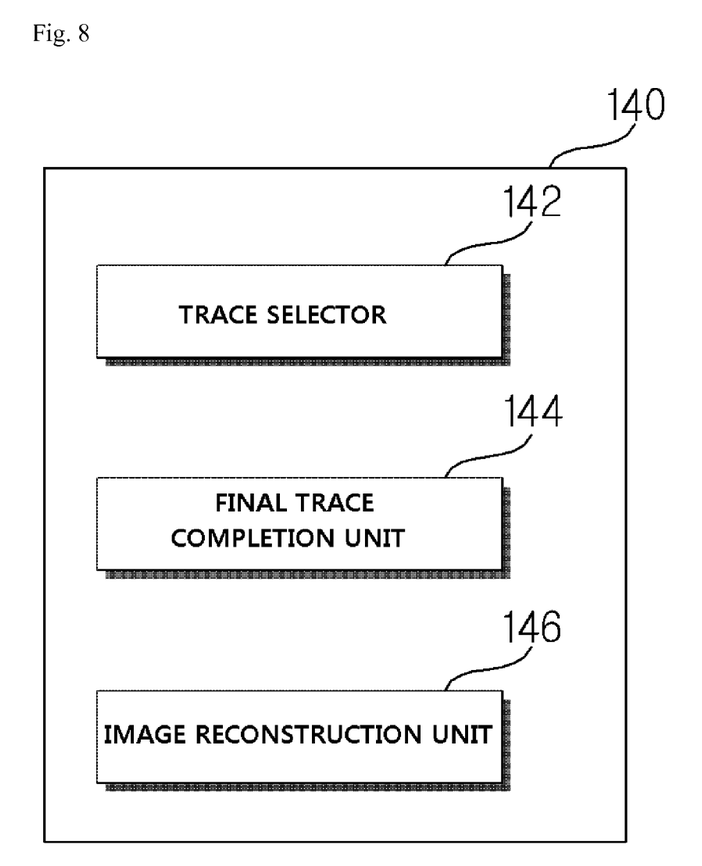
FIG. 8 is a block diagram illustrating a configuration of an image processor.

The image processor 140 may receive the images obtained by the image sensor 120, reconstruct the images for the image layer trace 14, and reconstruct the images as a panoramic image for the final trace. The image processor 140 may include a trace selector 142, a final trace completion unit 144, and an image reconstruction unit 146, as illustrated in FIG. 8. The trace selector 142 may divide each of the plurality of image layer traces 14a, 14b, and 14c into at least two sections and select an optimal image layer trace closed to a focal trace for each section, among the plurality of image layer traces 14a, 14b, and 14c belonging to each section. Here, the focal trace means a trace determined when a magnification of an image is adjusted to coincide with the position of the subject 10. The focal trace, which is a trace that most definitely shows the shape of the subject 10 and has the accurate geometrical information, means an image section essentially generated during the panoramic image photographing. In this case, as a method for selecting the section optimal image layer trace, various methods may be used, and preferably, the section optimal image layer trace is selected by frequency analysis. The final trace completion unit 144 may connect all of the selected section optimal image layer traces to complete the final trace. The image reconstruction unit 146 may reconstruct the panoramic images for the final trace.

The display unit 150 may output the panoramic images generated by the image processor 140 on a screen.

Meanwhile, the apparatus 100 for obtaining panoramic images in accordance with the embodiment of the present invention may further include a adjust module 160. The adjust module 160 may adjust the radiation irradiator 110 so as to irradiate the radiation for each section from a start point to an end point of the each image layer trace 14 and also may adjust the image sensor 120 so as to receive the irradiated radiation by interworking the radiation irradiator 110. In addition, when the radiation is irradiated on the ending section of the image layer trace 14, the adjust module 160 may recognize the irradiated radiation to determine that the final frame images 125 is photographed, thereby ending the photographing of the frame images 125. The adjust module may perform a process of allowing the radiation dose adjustor 130 and the image processor 140 to obtain the frame images 125 until the final frame images 125 are obtained.

Hereinafter, a method for obtaining panoramic images using the apparatus 100 for obtaining a panoramic image in accordance with the exemplary embodiment of the present invention will be described in detail with reference to FIG. 8. First, the average value calculator 132 included in the radiation dose adjustor 130 may calculate the gray scale average values of the pixels included in the predetermined reference area 126 in the frame image 125 obtained by irradiating the radiation on any one section of the plurality of image layer traces 14 where the region of interest of the subject 10 to be photographed is located (S100). Herein, each of the plurality of image layer traces 14 may be divided into at least two, preferably, 2800 sections.

Figure 9:
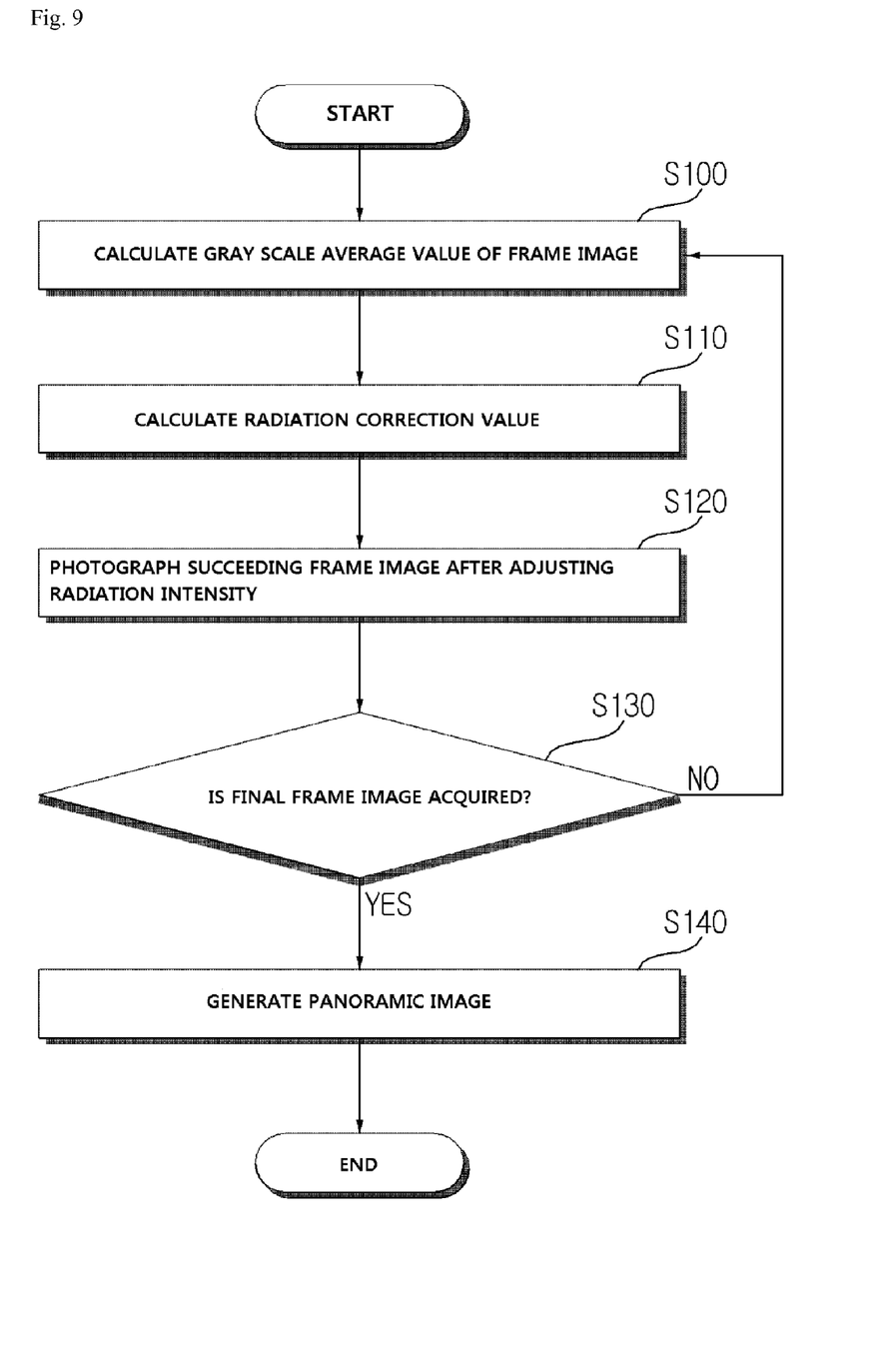
FIG. 9 is a flow chart illustrating a process of obtaining panoramic images in accordance with the exemplary embodiment of the present invention.
Figure 10:
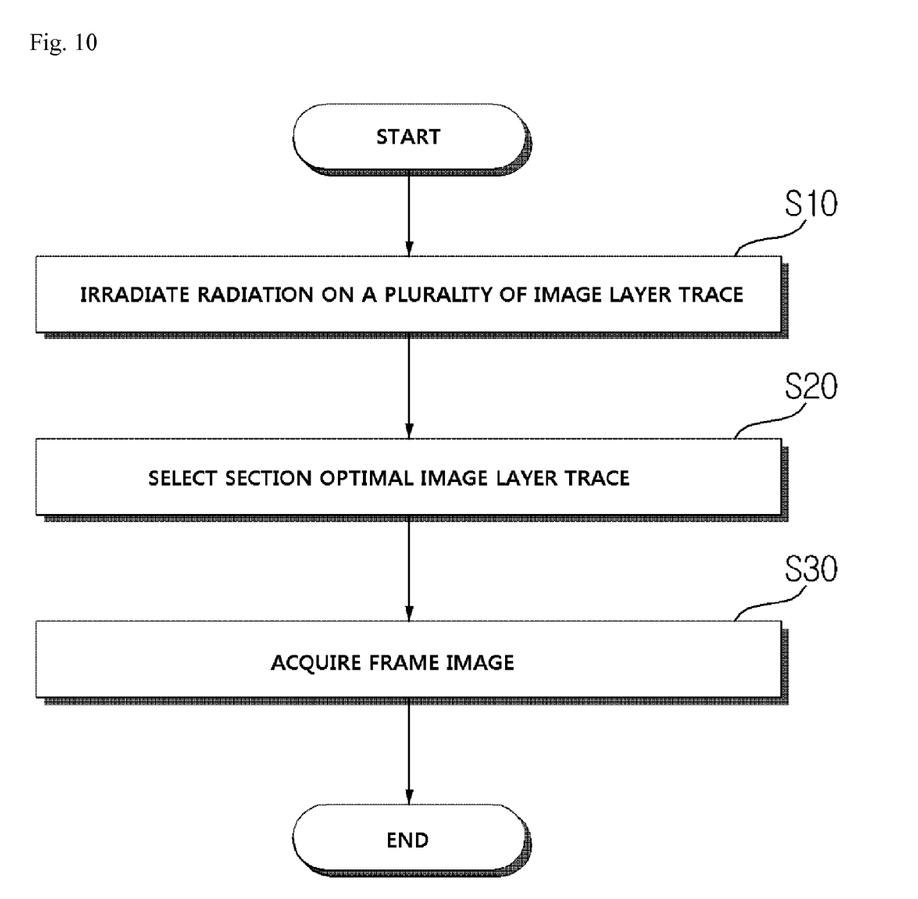
FIG. 10 is a flow chart illustrating a process of obtaining frame images.

The frame image 125 may be obtained according to a sequence illustrated in FIG. 9. That is, the radiation irradiator 110 may irradiate radiation, having a intensity predetermined by the intensity adjustor 136 included in the radiation dose adjustor, on any one section of the plurality of image layer traces 14 130 (S10), and the image processor 140 may select the section optimal image layer trace closest to the focal trace among the plurality of image layer traces 14a, 14b, and 14c of the corresponding section (S20). Then, the frame image 125 from the selected section optimal image layer may be obtained (S30).

In this case, when the obtained frame image 125 is the first frame image 125 for the start point section of the image layer trace 14, the intensity of the radiation irradiated from the radiation irradiator 110 for obtaining the first frame images 125, may be set according to the tube current or the tube voltage corresponding to the predetermined gray scale reference value by the radiation dose adjustor 130. In other words, the initial value of the intensity of the radiation irradiated on the start point section of the image layer trace 14 is determined according to the predetermined gray scale reference value. The gray scale average value of the obtained frame images 125 may be calculated by averaging the gray scale values of the pixels included in the reference area 126 of the obtained frame images 125, which is described above.

The correction value calculator 134 may determine whether a difference value obtained by subtracting the gray scale average value from the gray scale reference value calculated from the previously provided sample images deviates from the predetermined tolerable range and may calculate the radiation correction value corresponding to the difference value when the difference value deviates from the tolerable range (S110). Here, the sample images mean an image previously obtained by irradiating the radiation to various subjects 10 so as to set the gray scale reference value to be used to calculate the radiation correction value by comparing with the gray scale average value. The sample image may be provided in plural according to each category of the subject information including the age, weight, sex, nationality, race, occupation, and case history of the subject 10. The subject information may be discriminated in consideration of the fact that a thickness or a bone density of the cervical spine differently appears according to the age, weight, sex, or the like, of the subject 10 and may include factors affecting the thickness, the bone density, or the like, of the cervical spine in addition to the listed category. As such, various sample images are provided according to the category and thus, the gray scale reference value appropriate for various patients having different thickness or bone density of the cervical spine may be selectively applied.

The gray scale reference value is obtained by averaging the gray scale values of the predetermined sample area under the lower jaw in the sample images. In this case, the sample images may be a panoramic image obtained by reconstructing the images obtained in the frame unit and the position of the sample area may be preferably set at the same position as the position of the reference area 126 in the frame image 125. In addition, the predetermined area of the sample images is set to include only the remaining area other than the cervical portion from the sample images.

In order to assist the understanding, the process of determining the gray scale reference value is described in detail by way of example. However, it is assumed that the sample images are provided according to the ages in consideration of the fact that the bone density of the cervical portion differently appears according to the ages. First, 100 sample images for the arches of 20 and 25-years-old person are provided. In this case, one sample image is configured of 2800 frame unit images. Among them, if it is assumed that the frame unit images corresponding to the cervical portion is 800, the portion used to calculate the gray scale reference value among the sample images becomes the rest 2000 numbers other than 800 images corresponding to the cervical portion. The gray scale values of the pixels included in the sample area in 2000 frame unit images other than the cervical portion are averaged, and this process is performed on 100 sample images. Next, the average values obtained from each sample image are again averaged to calculate the gray scale reference value. The gray scale reference value may be provided in plural according to the age, weight, sex, nationality, race, occupation, and case history of the subject information and the correction value calculator 134 can set the gray scale reference value according to the corresponding category by selecting the category appropriate for the information on the patient to be photographed. In this case, the gray scale values of the pixels may be represented by brightness of 0 to 255 or 0 to 65535.

Hereinafter, a process of calculating the radiation correction value according to S110 is described by way of example. If the gray scale reference value is 150, the tolerable range for the difference value −10 to 10, and the gray scale average value of the frame image 125 is 130, the difference value becomes 20 and thus, deviates from the tolerable range set as the difference value of −10 to 10. In this case, the correction value calculator 136 calculates the radiation correction value corresponding to the difference value. Here, since the gray scale is linearly proportional to the radiation dose received in the image sensor 120, it is possible to calculate the radiation correction value for adjusting the radiation dose according to the difference value represented by the gray scale. The intensity adjustor 136 may receive the radiation correction value, adjust the tube current or the tube voltage of radiation to be applied to the other section adjacent to the previously photographed one section of the image layer trace 14 according to the calculated radiation correction value, and allow the radiation irradiator 110 to photograph the frame images succeeding to the obtained frame image by irradiating the intensity-adjusted radiation (S120).

Meanwhile, if it is assumed that the gray scale reference value and the conditions of the tolerable range are the same as the above description and the gray scale average value is 155, the difference value becomes −5 and thus, does not deviate from the tolerable range. In this case, the correction value calculator 136 may not calculate the radiation correction value. Therefore, the intensity adjustor 136 may apply the tube current or the tube voltage of the same amount as step S100 to the radiation irradiator 110, and the radiation irradiator 110 may irradiate the radiation having the same intensity as the radiation irradiated in the preceding section on the succeeding section of the image layer trace 14 to photograph the succeeding frame image 125.

The adjust module 160 determines whether the final frame images 125 for the end point section of the image layer trace 14 is obtained and the radiation irradiator 110, the image sensor 120, the radiation dose adjustor 130, and the image processor 140 repeatedly perform S100 to S120 until the final frame images 125 for the end point of the image layer trace 14 is obtained (S130). The adjust module 160 transmits all the frame images 125 obtained from the start point section to the end point section of the image layer trace 14 to the image processor 140 when the final frame image 125 are obtained, and the image processor 140 may link the received frame images 125 to generate the panoramic image (S140).

Figure 11:
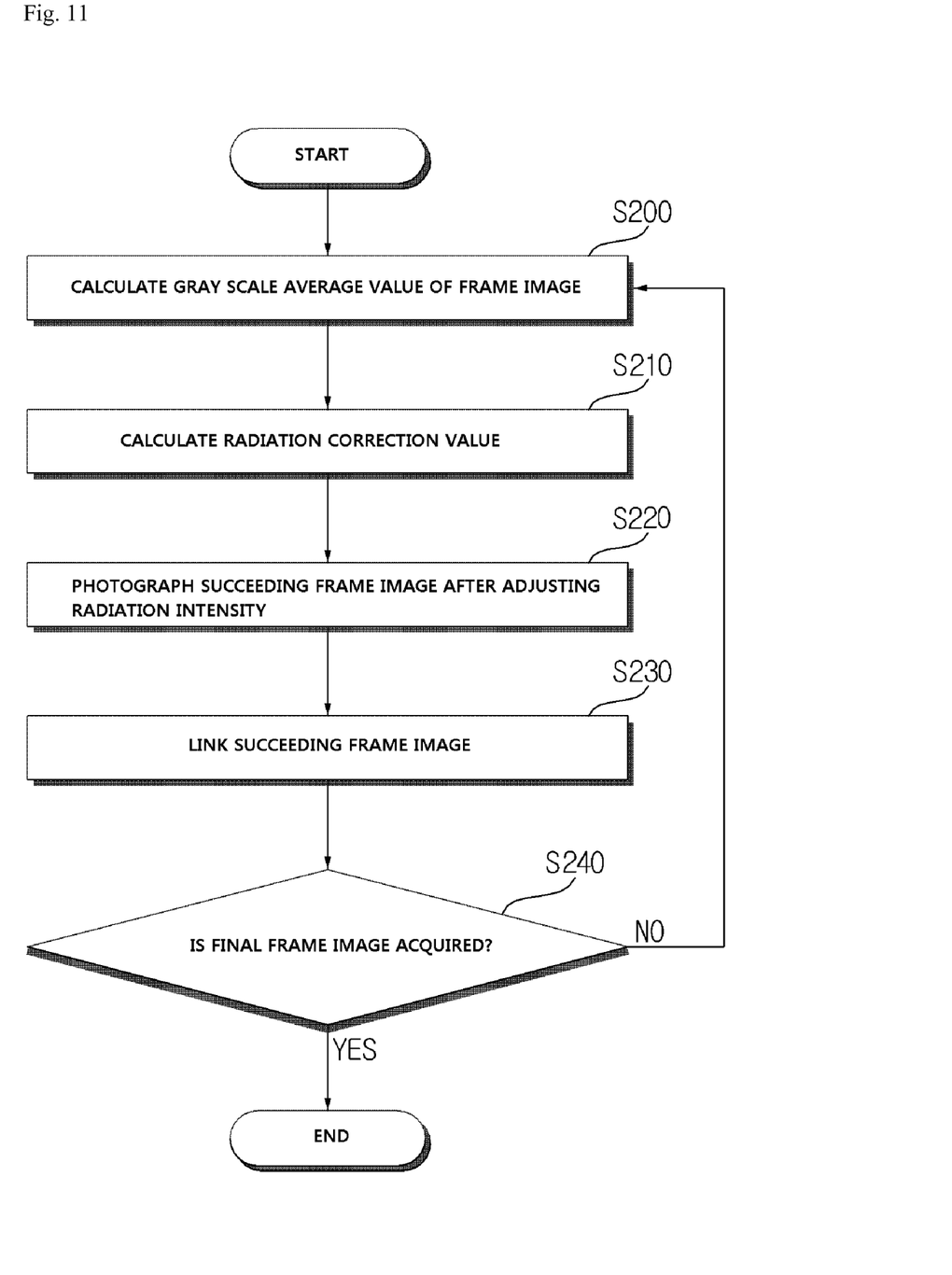
FIG. 11 is a flow chart illustrating a process of obtaining a panoramic image in accordance with the exemplary embodiment of the present invention.

FIG. 11 is a flow chart illustrating a process of obtaining a panoramic image in accordance with another embodiment of the present invention. In the method for obtaining the panoramic image illustrated in FIG. 11, S200 to S220 are the same as S100 to S120 in FIG. 8 and therefore, the description therefore will be omitted. At steps after S220, the image processor 140 may concatenate the succeeding frame image 125 for the succeeding section, adjacent to the preceding section, to the preceding frame images 125 for the preceding section of the image layer trace 14 (S230). In this case, the frame images corresponding to the optimal image layer traces of each section are concatenated with each other.

Next, the adjust module 160 may determine whether the final frame images 125 for the end point section of the image layer trace 14 are obtained and the radiation irradiator 110, the image sensor 120, the radiation dose adjustor 130, and the image processor 140 repeatedly perform S200 to S230 until the final frame images 125 for the end point section of the image layer trace 14 are obtained (S240). At S240, if it is determined that the adjust module 160 obtains the final frame images 125, a process of obtaining the frame images 125 ends, and the image processor 140 may obtain the panoramic image concatenated to the final frame image 125 during the repetitive execution of S200 to S230. The panoramic image generated by the same method, the cervical effect can be remarkably improved and the wholly uniform contrast can be implemented.

As described above, the present invention has been described merely in connection with the exemplary embodiments, and the skilled in this art can make modifications, variations and substitution without departing from the essential scope of the present invention. Accordingly, the exemplary embodiments and the drawing of this invention do not intend to limit but to explain the technical idea of this invention, and the scope of the technical idea of this invention is not limited to the embodiments and the drawings. The protection scope of the present invention should be interpreted with claims appended, and all technical ideas within equivalent scope with this invention should be in the protection scope of this invention.

INDUSTRIAL APPLICABILITY

The panoramic image representing the uniform contrast can be obtained by correcting the cervical effect.

The invention claimed is:

1. A method for obtaining panoramic images, comprising:
   a) obtaining a preceding frame image by irradiating radiation on any one section of an image layer trace in which a teeth trace of a subject is to be shaped;
   b) calculating a gray scale average value of pixels included in a predetermined reference area of the preceding frame image;
   c) comparing the calculated gray scale average value with a gray scale reference value calculated from a previously provided sample image, and generating a radiation correction value corresponding to a difference value; and
   d) obtaining a succeeding frame image by irradiating intensity-adjusted radiation on another section adjacent to the one section of the image layer trace according to the calculated radiation correction value.

2. The method of claim 1, wherein the gray scale reference value is calculated by averaging the gray scale values of the pixels included in a predetermined reference area of a part except a cervical portion among the sample image.

3. The method of claim 1, wherein the step d) includes
   d1) adjusting tube current or tube voltage according to the calculated radiation correction value; and
   d2) photographing the succeeding frame image by irradiating the intensity-adjusted radiation to the image layer trace according to the adjusted tube current or tube voltage.

4. The method of claim 1, further comprising: after the step d),
   obtaining a plurality frame images by repeating steps b) to d) until a final frame image for a final section of the image layer trace is obtained; and
   generating the panoramic images by reconstructing the plurality of obtained frame images.

5. The method of claim 1, further comprising: after the step d),
   e) linking the succeeding frame images to the preceding frame images; and
   generating the panoramic images by repeating steps b) to e) until a final frame image for a final section of the image layer trace is obtained.

6. The method of claim 1, wherein at the step c), when the difference value deviates from a predetermined tolerable range, the radiation correction value corresponding to the difference value is calculated.

7. The method of claim 6, wherein at the step c), when the difference value is in the tolerable range, at step d), the succeeding frame images are photographed by irradiating radiation having the same intensity as the radiation intensity irradiated at step a).

8. The method of claim 1, wherein the reference area is located under a lower jaw in the frame images.

9. The method of claim 1, wherein the image layer trace is provided in a plural by being divided into at least two sections, and
   wherein the obtaining of the preceding frame images includes:
      irradiating radiation on the plurality of image layer traces;
      selecting a section optimal image layer trace closed to a focal trace among the plurality of image layer traces belonging to each section; and
      obtaining the frame images for the selected section optimal image layer trace.

10. The method of claim 2, wherein the sample images are provided in plural according to each category of subject information including age, weight, sex, nationality, race, computation, and case history of the subject, and
    the gray scale reference value is selected from the plurality of gray scale reference values each calculated from the plurality of sample images.

11. An apparatus for obtaining panoramic images, comprising:
    a radiation irradiator to irradiate radiations to a plurality of image layer traces forming an irradiation trace of radiation for a subject;
    an image sensor to receive radiations transmitting the plurality of image layer traces to obtain frame images for the plurality of image layer traces;
    a radiation dose adjustor to receive the frame images from the image sensor, to calculate a radiation correction value for adjusting a intensity of radiation to be irradiated at the time of photographing succeeding frame images by using the received frame images, and to adjust tube current or tube voltage applied to the radiation irradiator according to the radiation correction value; and
    an image processor to generate a panoramic image of the image layer traces by receiving and reconstructing the frame images obtained from the image sensor.

12. The apparatus of claim 11, wherein the radiation dose adjustor includes:

an average value calculator to calculate a gray scale average value of pixels included in predetermined reference area among the obtained frame image;

a correction value calculator to compare the calculated gray scale average value with previously provided sample images and to calculate a radiation correction value corresponding to a difference value when the difference value deviates from a predetermined tolerable range; and an intensity adjustor to adjust tube current or tube voltage according to the calculated radiation correction value.

13. The apparatus of claim 11, wherein the image sensor is an area sensor that obtains images in a frame unit by intermittently irradiating radiation.

14. The apparatus of claim 11, further comprising:

an adjust module to adjust the radiation irradiator so as to irradiate the radiation on each section of the image layer trace and to adjust the image sensor so as to receive the irradiated radiation by interworking the radiation irradiator.

15. The apparatus of claim 11, wherein the image processor includes:

a trace selector to divide the plurality of image layer traces into at least two sections and to select, for each section, a section optimal image layer trace closed to a focal trace among the plurality of image layer traces belonging to each section;

a final trace completion unit to link all of the selected section optimal image layer traces to complete a final trace; and an image reconstruction unit to link the panoramic images for the final trace.

* * * * *